United States Patent [19]

Wheeler et al.

[11] 4,213,973
[45] Jul. 22, 1980

[54] USE OF OXADIAZOLE DERIVATIVES FOR CORN ROOT WORM CONTROL

[75] Inventors: Ronald E. Wheeler, Martinez; William F. King, Novato, both of Calif.

[73] Assignee: Chevron Research Company, San Francisco, Calif.

[21] Appl. No.: 943,079

[22] Filed: Sep. 18, 1978

[51] Int. Cl.² ............................................... A01N 9/36
[52] U.S. Cl. ................................................... 424/200
[58] Field of Search ........................................ 424/200

[56] References Cited

U.S. PATENT DOCUMENTS

| 3,973,011 | 8/1976 | Bohner et al. | 424/200 |
| 4,028,377 | 6/1977 | Meyer et al. | 424/200 |

Primary Examiner—V. D. Turner
Attorney, Agent, or Firm—D. A. Newell; T. G. DeJonghe

[57] ABSTRACT

A method for killing corn root worms which comprises applying to the soil habitat of the root worms an insecticidally effective amount of a compound of the formula

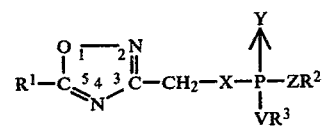

wherein $R^1$ is hydrogen or alkyl or alkoxy group of 1 to 6 carbon atoms; $R^2$ and $R^3$ are alkyl of 1 to 6 carbon atoms; and X, Y, Z and V are oxygen or sulfur.

2 Claims, No Drawings

USE OF OXADIAZOLE DERIVATIVES FOR CORN ROOT WORM CONTROL

RELATED APPLICATION

The present application is related to our concurrently filed application Ser. No. 943,078 entitled "Substituted Oxadiazoles and Their Use as Corn Root Worm Insecticides", the disclosure of which application is incorporated herein by reference.

BACKGROUND OF THE INVENTION

The present invention relates to certain oxadiazole derivatives and their use as corn root worm insecticides.

British Pat. No. 1,213,707 discloses insecticidal compounds of the general formula

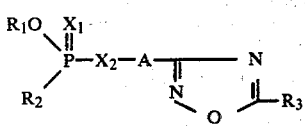

wherein $X_1$ and $X_2$, which may be the same or different, each represents an oxygen or sulfur atom; A represents an alkylene group; $R_1$ represents an alkyl group, $R_2$ represents an alkyl or alkoxy group; and $R_3$ represents a hydrogen atom or an optionally substituted carbamoyl or amino group. A particular species disclosed in the British patent at Table 2, 9th compound from the top, is 3-(diethoxyphosphinothioylthiomethyl)-5-methyl-1,2,4-oxadiazole.

The examples of the British patent show testing of certain of the compounds for insecticidal activity on adult houseflies; mosquito larvae, diamond back moth larvae, aphids and adult mustard beetles; red spider mites; and white butterfly larvae. None of these tests involved application and use of the insecticide in the soil habitat of the insects.

U.S. Pat. No. 4,028,377 discloses insecticidal compounds of the general formula

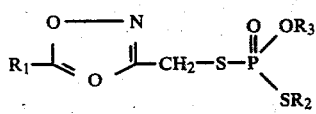

wherein $R_1$ represents hydrogen, unsubstituted alkyl, benzyl or phenyl, $R_2$ represents methyl or ethyl, and $R_3$ represents unsubstituted $C_1$-$C_7$ alkyl optionally interrupted by oxygen or represents $C_3$-$C_4$ alkenyl.

The examples of the U.S. Pat. No. 4,028,377 show testing of certain of the compounds for insecticidal activity on ticks in cotton wool; larvae of ticks; mites; and on root-gall-nematodes in soil. In the latter test, the soil infested with the root-gall-nematocides was treated with the compounds to be tested and then tomato seedlings were planted either immediately after the soil preparation or after 8 days waiting.

British Pat. No. 1,261,158 discloses compounds of the general formula

The first compound disclosed in Table I of British Pat. No. 1,261,158 is 5-(diethoxyphosphinothioylthiomethyl)-3-methylisoxazole. The compounds of the examples of British Pat. No. 1,261,158 were tested for insecticidal effectiveness on flies, mosquito larvae, moth larvae, mustard beetles, aphids, spider mites and butterfly larvae.

As described in the Ortho Seed Treater Manual, copyright 1976, Chevron Chemical Company, page 27, corn root worms have been controlled with chlorinated hydrocarbon insecticides, but in areas where resistance to such treatment has developed, good control has been obtained with organic phosphorus or carbamate soil insecticides such as Diazinon and Carbofuran insecticides. The chemical names and formulas for these latter insecticides is given below:

Diazinon insecticide: O,O-diethyl O-(2-isopropyl-4-methyl-6-pyrimidinyl)phosphorothioate

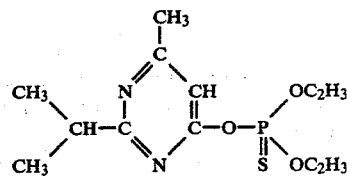

Carbofuran insecticide: 3,3-dihydro-2,2-dimethyl-7-benzofuranylmethylcarbamate

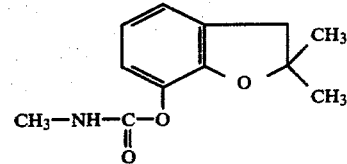

SUMMARY OF THE INVENTION

According to the present invention there is provided a method for killing corn root worms which comprises applying to the soil habitat of the root worms an insecticidally effective amount of a compound of the formula

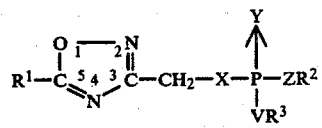

wherein $R^1$ is hydrogen or alkyl or alkoxy group of 1 to 6 carbon atoms; $R^2$ and $R^3$ are alkyl of 1 to 6 carbon atoms; and X, Y, Z and V are oxygen or sulfur.

According to another embodiment of the present invention a corn root worm insecticidal composition is provided which comprises a corn root worm-insecticidally effective amount of a compound in accordance with formula I above, and a biologically inert carrier. Preferably, the compound used in the insecticidal composition embodiment of the present invention is one in accordance with formula I above, wherein further $R^1$, $R^2$ and $R^3$ are $C_1$-$C_4$ alkyl; X and Z are sulfur; and Z and V are oxygen. Still further preferred is an insecticidal composition for corn root worm control wherein the compound used is further defined in that $R^1$ is methyl; and X is sulfur.

Among other factors, the present invention is based on our unexpected finding that compounds in accordance with the present invention have especially high activity against corn root worms when the compound is applied in the soil habitat of the corn root worm. term "corn root worm" is used herein to include the Northern, Southern and Western species of the corn root worm. All of these are of the Diabrotica genus. The scientific name of the Northern species is *Diabrotica longicornis*, the scientific name of the Southern species is *Diabrotica undecimpunctata howardi*, and the scientific name of the Western species is *Diabrotica virgifera*.

The compounds used in the method of the present invention or in the insecticidal composition of the present invention may be prepared as described in British Pat. No. 1,213,707 and U.S. Pat. No. 4,028,377, the disclosures of which references are incorporated herein by reference.

EXAMPLES

The substituted oxadiazole compounds were tested for control of corn root worm (Diabrotica larvae), by the following procedure:

A batch of 20 to 30 two-day-old Diabrotica eggs is placed on the bottom of a 237-cc clear plastic cup. These eggs are then covered with about 45 cc's of soil containing 15 ppm of the test compound. The soil is watered with 15 cc of water. The corn seeds, presoaked for 2 hours, are evenly distributed on the soil surface. Then an additional 45 cc's of the same treated soil is added to cover the seeds, and this soil is watered with an additional 15 cc's of water. The test cup is kept at 70° C. with occasional light watering just to keep the soil damp.

After 14 to 16 days, the test unit is examined under a dissecting scope, by observing the corn roots and larvae through the cup's clear plastic walls. Control of newly hatched larvae is rated by visually evaluating the degree of corn root damage by feeding larvae in conjunction with the visible presence of live and/or dead larvae.

The compounds tested and the percent control of Diabrotica larvae are given in Table I. Unless otherwise indicated, the tests were done using 15 ppm of the test compound, on the basis indicated above.

TABLE I

| Ex. No. | Compound | Control, % |
|---|---|---|
| 1 | 3-isopropyl-5-(methoxy-N-ethylamino-phosphinylthiomethyl)-1,2,4-oxadiazole | 0 |
| 2 | 3-(2'-pyridinyl)-5-(methoxy-N-ethylamino-phosphinylthiomethyl)-1,2,4-oxadiazole | 0 |
| 3 | 3-isopropyl-5-(diethoxyphosphinothioyl-thiomethyl)-1,2,4-oxadiazole | 100;98* |
| 4 | 3-(1'-cyclohexenyl)-5-(diethoxyphosphino-thioylthiomethyl)-1,2,4-oxadiazole | 0 |
| 5 | 3-(3',4'-dioxymethylenephenyl)-5-(di-ethoxyphosphinothioylthiomethyl)-1,2,4-oxadiazole | 0 |
| 6 | 3-(2,4-dichlorobenzyl)-5-(aminomethoxy-phosphinylthiomethyl)1,2,4-oxadiazole | 0 |
| 7 | 3-isopropyl-5-(aminomethoxyphosphinyl-thiomethyl)-1,2,4-oxadiazole | 0 |
| 8 | 3-isopropyl-5-(dimethoxyphosphinothioyl-thiomethyl)-1,2,4-oxadiazole | 95 |
| 9 | 3-(3'-nitrophenyl)-5-(dimethoxyphosphino-thioylthiomethyl)-1,2,4-oxadiazole | 0 |
| 10 | 3-isopropyl-5-(diethoxyphosphinothioyl-thioethylidene)-1,2,4-oxadiazole | 99.5*;100* 28*;22** |
| 11 | 3-(3'-nitrophenyl)-5-(diethoxyphosphino-thioylthiomethyl)-1,2,4-oxadiazole | 1* |
| 12 | 3-(3'-nitrophenyl)-5-(aminomethoxyphos-phinylthiomethyl)-1,2,4-oxadiazole | — |
| 13 | 3-methyl-5-(aminomethoxyphosphinylthio-methyl)-1,2,4-oxadiazole | 0* |
| 14 | 3-methyl-5-(diethoxyphosphinothioylthio-methyl)-1,2,4-oxadiazole | 100*;99** |
| 15 | 3-methyl-5-(dimethoxyphosphinothioyl-thiomethyl)-1,2,4-oxadiazole | 100*;99** 28* |
| 16 | 3-ethyl-5-(aminomethoxyphosphinylthio-methyl)-1,2,4-oxadiazole | 95*;95* |
| 17 | 3-ethyl-5-(dimethoxyphosphinothioylthio-methyl)-1,2,4-oxadiazole | 100*;98.5* |
| 18 | 3-ethyl-5-(diethoxyphosphinothioylthio-methyl)-1,2,4-oxadiazole | 100*;99.5* 98** |
| 19 | 3-(4'-nitrophenyl)-5-(dimethoxyphos-phinothioylthiomethyl)-1,2,4-oxadiazole | 0 |
| 20 | 3-tertiarybutyl-5-(aminomethoxyphos-phinylthiomethyl)-1,2,4-oxadiazole | 63 |
| 21 | 3-tertiarybutyl-5-(diethoxyphosphino-thioylthiomethyl)-1,2,4-oxadiazole | 99*;99.5* 0**;98** |
| 22 | 3-tertiarybutyl-5-(dimethoxyphosphino-thioylthiomethyl)-1,2,4-oxadiazole | 75*;95* 50 |
| 23 | 3-isopropyl-5-(methoxymethylthiophos-phinylthioethylidene)-1,2,4-oxadiazole | 25 |
| 24 | 3-heptyl-5-(diethoxyphosphinothioylthio-methyl)-1,2,4-oxadiazole | 0 |
| 25 | 3-(diethoxyphosphinothioylthiomethyl)-5-(diethoxyphosphinothioylthiomethyl)-1,2,4-oxadiazole | 0 |
| 26 | 3-(3'5'-dinotrophenyl)-5-(diethoxyphos-phinothioylthiomethyl)-1,2,4-oxadiazole | 0 |
| 27 | 3-methyl-5-diethoxyphosphinothioyloxy methyl)-1,2,4-oxadiazole | 96*;100* 100 |
| 28 | 3-tertiarybutyl-5-(dimethylaminomethoxy-phosphinylthiomethyl)-1,2,4-oxadiazole | 0 |
| 29 | 3-heptyl-5-(methylaminomethoxyphosphinyl-thiomethyl)-1,2,4-oxadiazole | 0 |
| 30 | 3-ethyl-5-(diethoxyphosphinothioylthio-ethyl)-1,2,4-oxadiazole | 0 |
| 31 | 3-(diethoxyphosphinothioylthiomethyl)-5-methyl-1,2,4-oxadiazole | 100;100* 100** |

*At 6.4 ppm of the test compound
**At 2.5 ppm of the test compound

We have found in our test work that certain relatively closely related compounds were not effective to control corn root worm. Those compounds showing little or no control above are excluded from the scope of the present invention. It may be noted that compounds within the scope of the present invention, in addition to being built from the oxadiazole ring, have a $CH_2$ linking group between the phosphorus-containing group and the oxadiazole ring, do not have H groups on the P atom, and have $R^1$ groups of no more than 1 to 4 carbon atoms.

The present invention is particularly directed to the use of compounds of the type shown by Example 31, for corn root worm control, as we have found these compounds to be especially effective for such use.

What is claimed is:

1. A method for killing corn root worms which comprises adding to the soil habitat of the root worms an insecticidally effective amount of a compound of the formula

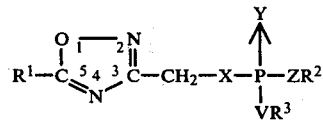

wherein $R^1$, $R^2$ and $R^3$ are $C_1$-$C_4$ alkyl; X and Y are sulfur; and Z and V are oxygen.

2. A method in accordance with claim 1 wherein $R^1$ is methyl, and X is sulfur.

* * * * *